United States Patent [19]

Müller et al.

[11] Patent Number: 5,215,751
[45] Date of Patent: Jun. 1, 1993

[54] THERAPEUTIC SYSTEM FOR THE RETARDED AND CONTROLLED TRANSDERMAL OR TRANSMUCOUS ADMINISTRATION OF ACTIVE SUBSTANCES (I)

[75] Inventors: Walter Müller, Neuwied; Heinrich Kindel, Rengsdorf, both of Fed. Rep. of Germany

[73] Assignee: LTS Lohmann Therapie Systeme GmbH & Co., Neuwied, Fed. Rep. of Germany

[21] Appl. No.: 478,811

[22] Filed: Feb. 12, 1990

[30] Foreign Application Priority Data

Feb. 18, 1989 [DE] Fed. Rep. of Germany ....... 3905051

[51] Int. Cl.$^5$ .............................................. A61F 13/00
[52] U.S. Cl. .................................. 424/443; 424/449; 424/448
[58] Field of Search ................ 424/447, 448, 449, 443

[56] References Cited

U.S. PATENT DOCUMENTS

| | | | |
|---|---|---|---|
| 4,756,710 | 7/1988 | Bondi et al. | 424/449 |
| 4,781,924 | 11/1988 | Lee et al. | 424/449 |
| 4,810,499 | 3/1989 | Nuwayser | 424/449 |
| 4,816,258 | 3/1989 | Nedberge et al. | 424/449 |

Primary Examiner—Thurman K. Page
Assistant Examiner—Leon R. Horne
Attorney, Agent, or Firm—Sprung Horn Kramer & Woods

[57] ABSTRACT

The present invention relates to a therapeutic system for the retarded and controlled transdermal and transmucous administration of active substances via an impermeable backing layer, an active substance containing reservoir, a substantially drug-free but drug-permeable layer, and a removable protective layer, whereby the drug-free layer is brought into contact with the active substance reservoir only immediately prior or after application and then lies between reservoir and application surface, whereby at least a portion of the active substance diffusing from the reservoir is converted in the retardation layer into a non-bioavailable form. In this connection, the conversion into the non-bioavailable form may be carried out either by immobilization of the active substance, by chemical reactions, or by physical interactions.

20 Claims, 1 Drawing Sheet

THERAPEUTIC SYSTEM FOR THE RETARDED AND CONTROLLED TRANSDERMAL OR TRANSMUCOUS ADMINISTRATION OF ACTIVE SUBSTANCES (I)

DESCRIPTION

The present invention relates to a device for the retarded and controlled transdermal or transmucous administration of active substances in form of a therapeutic system.

Therapeutic systems are drug-containing devices or forms of administration, respectively, which continuously release one or more pharmaceuticals at a predetermined rate over a fixed period of time to a fixed place of application (see Heilmann, "Therapeutische Systeme", Enke publishers, Stuttgart, 1984, page 24). A transdermal therapeutic system releases the active substance via the skin and thus is applied to the skin, i.e., topically.

The object when using active substances should always be to administer the active substance in an amount which, on the one hand, is as low as possible, and, on the other hand, promises the desired therapeutic effect at maximum certainty. For this purpose numerous, so-called therapeutic systems have been developed which release the active substance in a controlled manner predetermined by the system parameters. For many systemically effective active substances there is no need or desire to achieve evenly high plasma levels over the whole day.

For example, for some active substances it is of advantage, if the active substance levels are as low as possible during bedtime, and are increased to therapeutically necessary levels only at the end of the sleeping period.

This especially applies to nitro compounds for angina pectoris prophylaxis, since firstly angina pectoris attacks are rare during the night, but occur comparatively frequently in the early morning hours, and secondly the possible development of tolerance in connection with these nitro compounds may be avoided already by an interruption of medication for several hours. A dosage thus adapted to the needs would be desirable as well for nicotine, appetite-suppressing agents, blood pressure influencing agents ($\beta$-blockers), or antiasthmatics ($\beta$-sympathomimetics).

A dosage form providing this has to delay the active substance release to the organism for about 4-10 hours after administration in the evening so that therapeutically necessary plasma levels near the end of the sleeping period would arise without further activity of the patient.

The transdermal or transmucous administration of active substances is particularly suitable for such a relatively long retardation time. A transdermal system based on osmotic principles was described in U.S. Pat. No. 4,655,766, EP-A 0249475 described a system based on diffusional processes, and EP-A 0249343 described a system which is activated only on supply of liquids, such as e.g., cutaneous liquids.

Systems according to EP-A 0249475 in principle consist of two separate members, the actual active substance reservoir and an areal agent-free member. The drug-free layer is applied to the complete releasing surface of the reservoir prior to application, and then the system is applied to the skin with the other surface of this drug-free layer. Thus, a concentration gradient with respect to the active substance exists between both members of the system. According to the Fick laws, this results in the fact that the active substance diffuses into this layer which is free of active substance and, within a period of time defined by the system parameters, reaches the skin. Thus, the delay period corresponds to the time passed from the moment of combination of the two members of the system, which were separated prior to application, up to the moment at which the active substance is released to the skin in an amount sufficient for the therapeutical purpose.

In EP-A 0249475 two formulas are given for the calculation of this delay. Formula (1) is valid for a reservoir without membrane control $$T = L^2/6D \tag{1}$$

and formula (2) applies to a reservoir which is controlled by a membrane, i.e., a constant flux reservoir $$T = (L \times C)/(6 \times J) \tag{2}$$

T (h) delay period
L (cm) thickness of retardation layer
D (cm^2/h) Diffusion coefficient of active substance within the retardation layer
C ($\mu$g/cm^3) saturation concentration of active substance within the retardation layer
J ($\mu$g/h) Active substance flux from the reservoir According to formula (1) the thickness of the retardation layer and the diffusion coefficient of the active substance are available as parameters for influencing the delay time. A prolongation of the delay time is achieved by increasing the layer thickness and decreasing the diffusion coefficient.

Since the maximal flow capacity is calculated according to the following formula:

$$J(\max) = (D \times C)/L \tag{3}$$

it is demonstrated that a long retardation time automatically limits the active substance flux, if the release capacity of the reservoir is above the flow capacity of the retardation layer.

This is a great disadvantage which limits the use of such systems.

This disadvantage does not exist in systems according to EP-A 0249343.

Here, the active substance release from the reservoir is controlled by a membrane which, after a certain period of time subsequent to application of the system, highly increases its flow capacity by taking up activator liquid, and thus practically is switched from an impermeable membrane to one being permeable to the active substance. The activator liquid either is the cutaneous moisture itself, a liquid into which the system is dipped prior to use, or which the system contains in a separate reservoir and which is released only on additional manipulation.

However, the disadvantage of these systems is the fact that it is difficult to to control the permeability of a membrane with respect to the necessary amount in time by a preprogrammed manner. This particularly applies to that case where cutaneous liquid is used as activator liquid. In this case, great individual differences and parameters difficult to control, e.g., room temperature, clothings, play an important role and they uncontrollably influence the length of retardation time and the active substance flux from the system.

It was accordingly the object of the present invention to develop systems for the retarded transdermal or transmucous administration of active substances, which systems combine the high reliability of function of the systems according to EP-A 0249475 with the advantage of an active substance flux which is only slightly influenced by the delay element of the systems according to EP-A 0249343.

Surprisingly, this object was achieved in that an auxiliary agent was incorporated into the drug-free retardation layer, which auxiliary up to its exhaustion or until an equilibrium is achieved converts the active substance into a non-bioavailable form. As a matter of fact, this drug-free retardation layer may be brought into contact with the active substance reservoir only immediately prior or after application, and is located after application between reservoir and skin or mucosa, respectively.

This can be achieved, e.g., in that at first the retardation layer is applied to the site of application and then the reservoir is applied thereto, or in that the complete system is produced immediately prior to application, as is described in EP-A 0249475.

Equations 1 and 2 show that the retardation time is proportional to the square of the layer thickness, or directly proportional to the layer thickness, respectively. On the other hand, equation 3 clearly shows that the maximum flow capacity of a layer is inversely proportional to the layer thickness.

This means that the flow capacity becomes the lower the longer the delay time shall be.

Due to the fact that a portion of the active substance penetrating the retardation layer is converted into a non-bioavailable form-and this, as a matter of fact, is that active substance portion diffusing at first-a long retardation time is obtained, avoiding relatively thick retardation layers associated with a decreased flow capacity.

Systems according to the present invention in principle offer two possibilities to convert the active substance into a non-bioavailable form: a. the active substance is immobilized b. the active substance is converted into a salt The active substance is immobilized, if it is bonded to a polymer which itself is not able to diffuse. This is the case, if the active substance is an acid or a base and is bonded to a polymeric polybase or polyacid in the retardation layer. In this connection, the active substance is converted into a polymeric salt by a simple acid-base-reaction and cannot leave the system in this form.

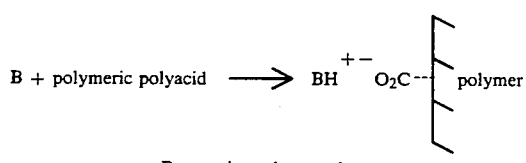

B = active substance base

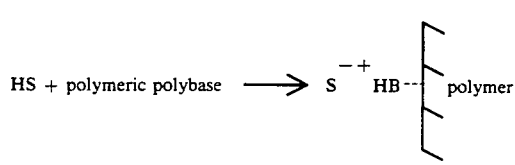

S = active substance acid

But even if the active substance itself is present as a salt which is able to penetrate into the skin, it can be immobilized, if the effective ion is exchanged for an uneffective one by an ion exchanger.

Those auxiliaries which are able to absorb substances at their surfaces by physical interactions react unspecifically. Those substances, e.g., are silica gel or aluminium oxide which are frequently used in chromatography due to these capacities.

Particularly in case of the transdermal application of active substances, the lipophilic barrier of the stratum corneum is to be passed. This naturally is particularly difficult for substances of polar or ionic nature. Since most active substances are either bases or acids themselves, it is easily possible to render them so hydrophilic by salt formation in the retardation layer that they are able to diffuse within the system as then ionic compounds, but that they may no longer pass the stratum corneum and thus are no longer bioavailable.

It is characteristic of all these reactions that the auxiliaries reacting with the active substances in the retardation layer do so only until they are either exhausted or an equilibrium is achieved. Not until this moment active substance even in bioavailable form reaches the site of application, i.e., the skin or mucosa.

Thus, the retardation time is essentially determined by the delivery capacity of the active substance reservoir, on the one hand, and the amount of auxiliary reacting with the active substance in the retardation layer, on the other hand. It is easily possible to prolong the retardation time by increasing the auxiliary concentration with the layer thickness remaining constant. As a matter of fact, both the reservoir and the retardation layer may be built up as complicated as desired, e.g., be multi-layered. It may be of advantage, e.g., to insert active substance flux controlling membranes between active substance reservoir and retardation layer and/or between retardation layer and site of application.

It may be suitable, too, to use non-adhesive or only poorly adhesive layers which must be provided with additional self-adhesive films, if necessary.

All materials may be used as materials for the reservoirs or backing layers, respectively, and for the removable protective layer, which are commonly employed for the production of transdermal and transmucous systems and which are sufficiently known to the man skilled in the art.

Suitable materials for the backing layer, e.g., are foils of polyester, PVC, polyamide, polyethylene, or polypropylene. Commonly used as well are composite foils of these materials, whereby an additional aluminium layer frequently provides for the impermeability to active substances. In principle the same materials as used for the backing layer are suitable materials for the protective layer, however, in addition they have to be rendered dehesive.

As basic materials for the reservoirs the following materials are mentioned as examples: polyisobutylene, styreneisoprene-styrene blockcopolymers, polysiloxanes, polymethacrylates, polyurethanes, polyesters, polyamides, and copolymers of ethylene with, e.g., vinylacetate or acrylic acid derivatives.

BRIEF DESCRIPTION OF THE DRAWING

The invention is further illustrated by FIG. 1 and the following example, whereby in FIG. 1 (1) represents the impermeable backing layer, (2) the active substance containing reservoir layer, and (3) the drugfree retardation layer.

EXAMPLE

| Production of the active substance reservoir | |
| --- | --- |
| 300 g | of a 20% solution of Oppanol B100 (polyisobutylene, medium molecular weight 1 270 000) |
| 108 g | of a 50% solution of Abitol (hydrogenated abietyl alcohol) and |
| 108 g | of a 50% solution of Piccotac C-BHT (hydro- and carbon resin) in benzine and |
| 12 g | Miglyol 812 | are mixed, homogenized and subsequently 169 g lactose (EP D80 of Messrs. Meggle) having a nitroglycerine load of 10% are added under stirring.

Using this mass a film having a thickness of 350μ is applied to siliconized kraft paper, the solvent is removed by drying at 50° C. for 20 minutes. The dry film exhibits a weight per unit area of 220 g/m².

Due to its high content of lactose this reservoir film adheres relatively poorly so that an adhesive film having an area weight of 20 g/m² has to be laminated prior to the application of the aluminized carrier foil of polyester. This adhesive film does not contain lactose, for the rest, however, is identical to the composition of the reservoir.

| Production of the retardation layer | |
| --- | --- |
| 300 g | of a 20% solution of Oppanol B100, |
| 108 g | of a 50% solution of Abitol and |
| 108 g | of a 50% solution of Piccotac C-BT in benzine and |
| 159 g | benzine are mixed homogenized and subsequently |
| 44 g | silica gel 60 H for thin-layer-chromatography |

(Messrs. Merck, Darmstadt) are added under stirring. Using this mass a film having a thickness of 250μ is applied to a siliconized kraft paper and dried at 50° C. for 20 minutes. The dry film has an area weight of 54 g/m². This film, too, is of poor adherence due to its high solids content so that a film of improved adherence and same composition, however without silica gel, and a weight per unit area of 20 g/m² has to be laminated. The laminate is covered with an aluminized and siliconized polyester foil having a thickness of 100μ, this foil being the removable protective layer.

Conduct of the in-vitro-release

Figure 1:
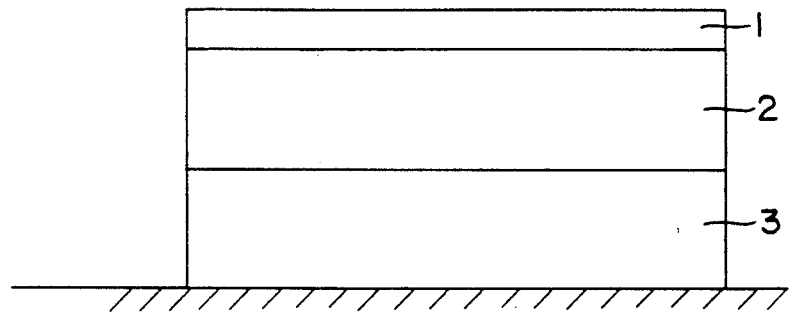
Figure 2:
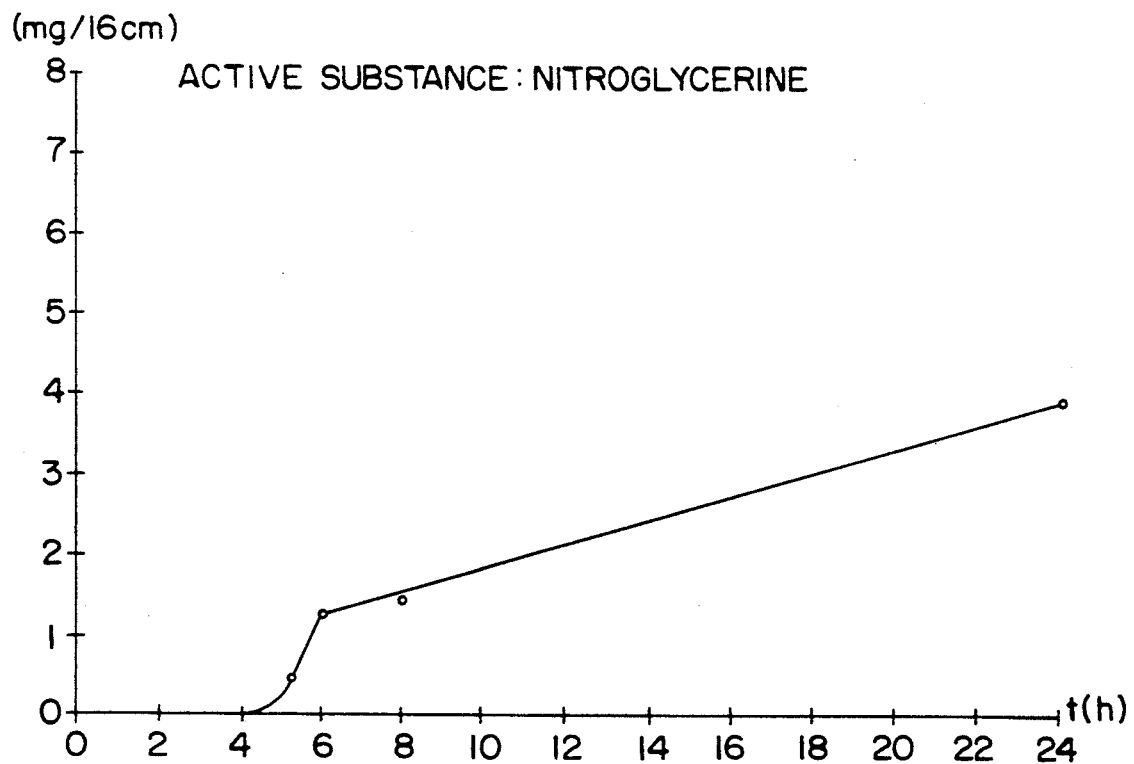
FIG. 2 is a graph showing the course of the drug release

Immediately prior to the test start reservoir, layer and retardation layer were laminated and cut into single pieces of 16 cm². The in-vitro-release was carried out in a rotating bottle apparatus at 32° C. using 100 ml physiological saline as release medium. The samples were measured by means of a HPLC-method. The course of the release is shown in FIG. 2. It can clearly be recognized that not until 5 hours a noticeable active substance flux starts.

We claim:

1. A therapeutic system for the retarded and controlled transdermal or transmucous administration of active substances, comprising an impermeable backing layer, an active substance-containing reservoir layer, a substantially drug-free but drug-permeable layer, and a removable protective layer, whereby the drug-free layer is separated from the active substance containing reservoir before application to an application surface and in direct contact with the active substance containing reservoir layer during the period of application to said application surface, the removable protective layer being present on the outside of the drug-free but drug-permeable layer before application to said application surface, after application to said application surface at least a portion of the active substance being present within the drug-free but drug-permeable layer in a non-bioavailable form.

2. The therapeutic system according to claim 1, wherein the active substance is a base and the drug-free layer includes an acid.

3. The therapeutic system according to claim 1, wherein the drug-free layer comprises an acidified buffer.

4. The therapeutic system according to claim 1, wherein the active substance is an acid and the drug-free layer includes a base.

5. The therapeutic system according to claim 4, wherein the base is a polymeric base.

6. The therapeutic system according to claim 1, wherein the drug-free layer comprises a basified buffer.

7. The therapeutic system according to claim 1, wherein the active substance is a salt and the drug-free layer includes an ion exchanger.

8. The therapeutic system according to claim 1, wherein the drug-free layer comprises an auxiliary agent which can absorb a portion of the active substance by physical interaction.

9. The therapeutic system according to claim 8, wherein said auxiliary agent is a silica gel, a silica gel derivative, an aluminum oxide, active carbon, titanium dioxide, zinc oxide, magnesium oxide, lactose, or a cellulose derivative.

10. The therapeutic system according to claim 1, wherein the active substance is an organic nitro compound.

11. The therapeutic system according to claim 1, wherein the active substance is nicotine.

12. The therapeutic system according to claim 1, wherein the active substance is an appetite-suppressing agent.

13. The therapeutic system according to claim 12, wherein the appetite-suppressing agent is norpseudoephedrine, amfepramone, mefenorex, propylhexedrine, fenfluramine, or mazindol.

14. The therapeutic system according to claim 1, wherein the active substance is a beta-blocker.

15. The therapeutic system according to claim 14, wherein the beta-blocker is alprenolol, oxprenolol, penbutolol, bupranolol, metoprolol, betaxolol, atenolol, acetubolol, metipranolol, propranolol, nadolol, pindolol, mepindolol, carteolol, carazolol, timolol, or sotalol.

16. The therapeutic system according to claim 1, wherein the active substance is an α-sympathomimetika.

17. The therapeutic system according to claim 16, wherein the active substance is norfenefrine, octapamine, oxedrine, metaraminol, midodrine, or oxilofrine.

18. The therapeutic system according to claim 1, wherein the active substance is a β-sympathomimetika.

19. The therapeutic system according to claim 18, wherein the active substance is salbutamol, terbutaline, fenoterol, clenbuterol, reproterol, hexoprenaline, bamethan, or isoxsuprine.

20. A therapeutic system for the retarded and controlled transdermal or transmucous administration of a drug, comprising
- A) an impermeable backing layer in use spaced from the skin,
- B) a drug containing reservoir layer adjacent the backing layer,
- C) a substantially drug-free but drug-permeable layer separated from the reservoir layer until use, the drug-free permeable layer containing a retardant for binding with the drug, in use the drug permeable layer contacting the skin, and
- D) a removable protective layer on the drug permeable layer, the user removing the protective layer and placing the drug-free permeable layer against the skin and placing the reservoir layer in contact with the drug-free permeable layer, whereby initially drug from the reservoir enters the layer (C) but is bound therein by the retardant so the drug does not initially pass through (C) to the skin, but, after a period of time the drug then passes through (C) to the skin.

* * * * *